United States Patent [19]

Southgate et al.

[11] 4,428,961

[45] Jan. 31, 1984

[54] β-LACTAM CONTAINING COMPOUNDS, THEIR PREPARATION AND USE

[75] Inventors: Robert Southgate, Warnham; Terence C. Smale, Epsom Downs; Roger J. Ponsford, Horsham, all of England

[73] Assignee: Beecham Group Limited, England

[21] Appl. No.: 227,765

[22] Filed: Jan. 23, 1981

[30] Foreign Application Priority Data

Jan. 25, 1980 [GB] United Kingdom ................. 8002565

[51] Int. Cl.³ .................... A61K 31/40; D09D 487/04

[52] U.S. Cl. ............................... 424/274; 260/239 A; 260/245.2 T; 424/114

[58] Field of Search .................. 260/245.2 T; 424/274

[56] References Cited

U.S. PATENT DOCUMENTS

| | | | |
|---|---|---|---|
| 4,141,986 | 2/1979 | Cassidy et al. | 260/245.2 T |
| 4,146,610 | 3/1979 | Cole et al. | 260/245.2 T |
| 4,255,441 | 3/1981 | Ponsford et al. | 260/245.2 T |
| 4,263,314 | 4/1981 | Ponsford et al. | 260/245.2 T |

*Primary Examiner*—Mary C. Lee

*Attorney, Agent, or Firm*—Jacobs & Jacobs

[57] ABSTRACT

The present invention provides a compound of formula (I):

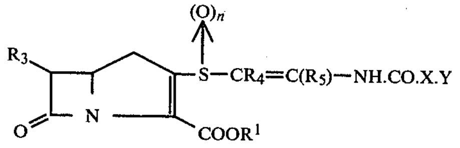

wherein $R^1$ is a group such that $COOR^1$ is a carboxyic acid group or a salt or ester thereof;

$R^3$ is hydrogen or an organic radical;

n is zero or 1;

$R^4$ and $R^5$ are independently hydrogen or $C_1$-$C_3$ alkyl;

X is $C_1$-$C_6$ alkylene optionally substituted by hydroxy or a carboxylic acid group or a salt or ester thereof;

Y is an amino, or substituted amino, wherein the substituent is carboxylic acyl, $C_1$-$C_6$ alkyl or a group $=C(R^{14})NR^{15}R^{16}$ wherein $R^{15}$ and or $C_1$-$C_6$ alkyl and $R^{14}$ is hydrogen or $C_1$-$C_6$ alkyl, or a group $-NR^AR^B$ wherein $R^A$ and $R^B$ are independently hydrogen or $C_1$-$C_6$ alkyl.

66 Claims, No Drawings

β-LACTAM CONTAINING COMPOUNDS, THEIR PREPARATION AND USE

The present invention relates to β-lactam containing compounds, to their preparation and to their use in antibacterial pharmaceutical compositions.

Our co-pending European Patent Application Number 79301458.0, U.S. Ser. No. 059,463 and Japanese Patent Application Number 95967/79 all disclose a distinct class of synthetic antibacterial agents. The present invention provides a compound of formula (I):

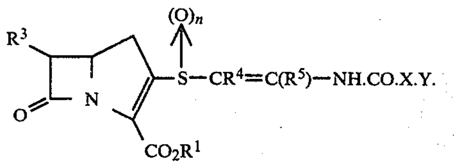

(I)

wherein $R^1$ is a group such that $CO_2R_1$ is a carboxylic acid group or a salt or ester thereof;
$R^3$ is hydrogen or an organic radical;
n is zero or 1;
$R^4$ and $R^5$ are independently hydrogen or $C_{1-3}$ alkyl;
X is $C_{1-6}$ alkylene optionally substituted by hydroxy or a carboxylic acid group or a salt or ester thereof;
Y is amino, or substituted amino, wherein the substituent is carboxylic acyl, $C_{1-6}$ alkyl or a group $=C(R^{14})NR^{15}R^{16}$ where $R^{15}$ and $R^{16}$ are independently hydrogen or $C_{1-6}$ alkyl, and $R^{14}$ is a hydrogen, $C_{1-6}$ alkyl, or a group $-NR^AR^B$ wherein $R^A$ and $R^B$ are independently hydrogen or $C_{1-6}$ alkyl.

When $R^3$ is an organic radical it may represent a hydrocarbon group of up to 10 carbon atoms, optionally substituted with a functional substituent.

Suitably $R^3$ is hydrogen or a group of formula (c):

$$-CR^6R^7R^8 \qquad (c)$$

where $R^6$ is hydrogen, hydroxy, a group $-OSO_3H$ or a pharmaceutically acceptable salt thereof, $-O-COR°$ or $-OCO_2R°$ where R° is a $C_{1-8}$ hydrocarbon optionally substituted with halogen, $C_{1-6}$ alkoxy, or nitro;
$R^7$ is hydrogen or $C_{1-3}$ alkyl;
$R^8$ is hydrogen or $C_{1-3}$ alkyl.

One sub-class of compounds of this invention comprises compounds of formula (II):

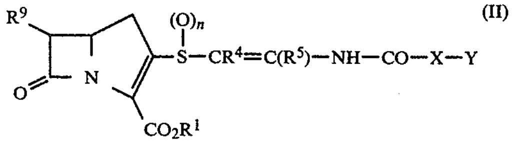

(II)

wherein n, $R^1$, $R^4$, $R^5$ and X are as defined with reference to formula (I); $R^9$ is a hydrogen atom or group of the sub-formula:

$$-CR^{10}R^{11}R^{12}$$

wherein $R_{10}$ is a hydrogen atom or a hydroxy, $OCOR^{13}$ or $OCOOR^{13}$ group where $R^{13}$ is a $C_{1-3}$ alkyl, phenyl, benzyl, fluorobenzyl, chlorobenzyl, bromobenzyl, $C_{1-3}$ alkoxybenzyl or nitrobenzyl group; $R^{11}$ is a hydrogen atom or a $C_{1-3}$ alkyl group; $R^{11}$ is a hydrogen atom or a $C_{1-3}$ alkyl group; and Y is amino, $C_{1-6}$ alkylamino, a protected amino group, an acylamino group —NHCOZ wherein Z is a lower alkyl, aryl aryloxyalkyl or aralkyl group, or Y is a $N=C(R^{14})-NR^{15}R^{16}$ group, wherein $R^{14}$ is a hydrogen atom or an alkyl group of 1 to 6 carbon atoms, $R^{15}$ is a hydrogen atom or an alkyl group of 1 to 6 carbon atoms and $R^{16}$ is a hydrogen atom or an alkyl group of 1 to 6 carbon atoms.

Suitably n is zero.

Suitably $C_{1-3}$ alkyl groups include methyl, ethyl, n-propyl and iso-propyl of which methyl and ethyl are the more suitable values and methyl is the preferred value.

It will be realised that the compounds of the formula (I) may be in either of two geometrical forms about the exocyclic carbon-carbon double bond as shown in the sub-formulae (d) and (e) thus.

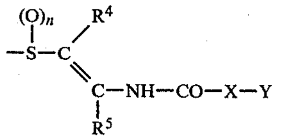

(d)

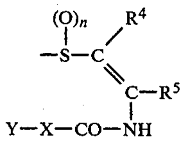

(e)

Both separated geometrical isomers and mixtures of said isomers are within the scope of this invention.

Aptly $R^3$ is a hydrogen atom.

Apt groups of the sub-formula (c) include those of the sub-formulae (f), (g), (h) and (i):

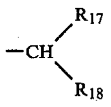

(f)

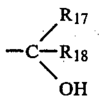

(g)

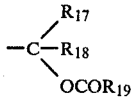

(h)

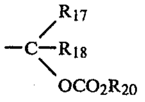

(i)

wherein $R_{17}$ is a hydrogen atom or a methyl or ethyl group; $R_{18}$ is a hydrogen atom or a methyl or ethyl group; $R_{19}$ is a lower alkyl group; $R_{20}$ is a benzyl, fluorobenzyl, chlorobenzyl, bromobenzyl, lower alkylbenzyl or nitrobenzyl group.

Favourably $R_{17}$ is a hydrogen atom. Favourably $R_{19}$ is a methyl or ethyl group. Favourably $R_{20}$ is a benzyl or p-nitrobenzyl group. Preferably $R_{19}$ is a methyl group. Preferably $R_{20}$ is a p-nitrobenzyl group.

Specific groups $R^3$ include the methyl, ethyl, iso-propyl, n-propyl, α-hydroxyethyl, α-hydroxypropyl, α- acetoxyethyl, α-acetoxypropyl, 2-hydroxy-2-propyl, α-propionoxyethyl and α-p-nitrobenzyloxycarbonyloxyethyl groups.

$R^4$ is suitably a lower alkyl group as hereinbefore defined. $R^4$ is preferably a hydrogen atom.

$R^5$ is suitably a lower alkyl group as hereinbefore defined. $R^5$ is preferably a hydrogen atom.

X is a branched alkylene group or a straight-chained alkylene group of 1 to 6 carbon atoms optionally substituted by a hydroxy group or carboxylic acid group or a salt or ester thereof. Thus suitable values of X include methylene, ethylene, trimethylene, propylene, 1,1-dimethylmethylene, 1-methylmethylene, tetramethylene, 1-methyltrimethylene, 2-methyltrimethylene, 3-methyltrimethylene, 1-ethylmethylene, 1-propylmethylene, 1-butylmethylene, 1-ethylethylene, 2-ethylethylene, pentamethylene and hexamethylene. Further suitable values of X are those wherein the alkylene group is substituted with a hydroxy group for example 1-hydroxyethylene, 2-hydroxyethylene, 1-hydroxypropylene, 2-hydroxypropylene and hydroxymethylmethylene. Still further suitable values of X are those wherein the alkylene group is substituted with a carboxylic acid group or salt or ester thereof for example 2-carboxyethylene, 2-carboxypropylene, 3-carboxypropylene, 2-carboxytrimethylene and 3-carboxytrimethylene.

Favourably X is methylene, ethylene, propylene, 1-propylmethylene, 1-butylmethylene, trimethylene, 2-carboxyethylene, 2-carboxypropylene, 3-carboxypropylene or hydroxymethylmethylene.

A preferred value of X is methylene

A further preferred value of X is ethylene.

Suitably Y is an amino group ($-NH_2$). Suitably also Y is a substituted amino group such as $C_{1-6}$ alkylamino or di($C_{1-6}$) alkylamino, for example methylamino, ethylamino or propylamino. Alternatively Y is a protected amino group wherein the protecting group is one known in the art to be readily removable, such as p-nitrobenzyloxycarbonyl which is removable on catalytic hydrogenation.

Suitably also Y is a carboxylic acyl amino group such as a $C_{1-6}$ alkylamido group (preferably a $C_{1-3}$ alkylamido group), for example acetamido and propionamido, an arylamido group such as benzamido, an aryloxy ($C_{1-3}$) alkyl group such as phenoxyacetamido, or an aryl ($C_{1-3}$) alkyl group such as phenylacetamido.

When used herein "aryl" means a phenyl group optionally substituted by chloro, bromo, fluoro, nitro, $C_{1-3}$ alkyl or $C_{1-3}$ alkoxy. Thus suitable values for aryl ($C_{1-3}$) alkyl include benzyl, phenylethyl, bromobenzyl, chlorobenzyl, fluorobenzyl, nitrobenzyl, $C_{1-3}$ alkylbenzyl and $C_{1-3}$ alkoxybenzyl.

Preferred examples of carboxylic acyl amino include acetamido, propionamido, benzamido, phenylacetamido and phenoxyacetamido.

Aptly Y is a $-N{=}C(R_{14})NR_{15}R_{16}$ group wherein $R_{14}$, $R_{15}$ and $R_{16}$ are as defined in relation to formula (I).

More aptly $R_{14}$ is a hydrogen atom or methyl, or ethyl group, $R_{15}$ is a hydrogen atom or methyl or ethyl group; and $R_{16}$ is a hydrogen atom or methyl or ethyl group. Favourably $-N{=}C(R_{14})NR_{15}R_{16}$ is selected from $-N{=}CHNH_2$, $-N{=}C(CH_3)NH_2$, $-N{=}C(CH_3)NH_2$, $-N{=}C(C_2H_5)NH_2$, $-N{=}CHNHCH_3$, $-N{=}CHN(CH_3)_2$, $-N{=}C(CH_3)NHCH_3$, $-N{=}CHNHC_2H_5$, $-N{=}CHNHC_3H_7$ and $-N{=}CHNC_4H_9$.

It is to be realised that $-N{=}C(R_{14})NR_{15}R_{16}$ when at least one of $R_{15}$ and $R_{16}$ is a hydrogen atoms may be written in the form $-NHC(R_{14}){=}NR_{15}$ for example.

In a further aspect $-N{=}C(R_{14})NR_{15}R_{16}$ may be a guanidine of the sub-formula $-N{=}C(NR^AR^B)NR_{15}R_{16}$; favourably $R^A$ and $R^B$ are independently selected from hydrogen, methyl, ethyl, propyl or butyl.

The compounds of the formula (II) wherein $CO_2R_1$ is a carboxylic acid group or salt thereof are thus particularly suitable. When Y contains an amino or an imino group the compound of the formula (I) is zwitterionic. When Y does not contain an amino or imino group it is preferred that $CO_2R_1$ is a carboxylic acid group salted by a pharmaceutically acceptable cation such as those of the alkali or alkaline earth metals or a non-toxi amine. Favoured salts include the sodium and potassium salts.

In addition the group X may contain a carboxylic acid group or salt or ester thereof in which case a di-acid, di-salt, di-ester or mono-salt-mono-ester of the compound of the formula (I) may be formed. If $CO_2R_1$ represents a carboxylic ester then it is preferred that the group X contains a carboxylic acid or salt thereof; if the group Y contains an amino or imino group then a zwitterion of the compound of the formula (I) is formed; if the group Y does not contain an amino or imino group and a carboxylic acid or salt or ester thereof is present in the group X then it is preferred that the carboxylic acid group is salted by a pharmaceutically acceptable cation as hereinbefore described with reference to the group $CO_2R_1$.

Compounds of the formula (I) wherein $CO_2R^1$ is an ester group have activity in their own right. It is often preferred however that esters of this invention are those which are convertible to a corresponding salt by chemical or biological means. If a di-ester of a compound of the formula (I) is formed then it is preferred that at least one of the ester groups is convertible to a corresponding salt by chemical or biological means.

Suitably the esterifying radical is a group of the sub-formulae (j), (k), (l) or (m):

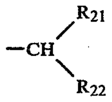
(j)

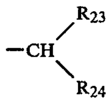
(k)

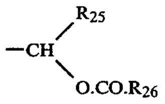
(l)

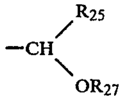
(m)

wherein $R_{21}$ is a hydrogen atom or an alkyl, alkenyl or alkynyl group of up to 3 carbon atoms; $R_{22}$ is a hydrogen atom or a methyl group; $R_{23}$ is a phenyl group or a phenyl group substituted by a fluorine, chlorine or bromine atom or a nitro, methyl or methoxyl group; $R_{24}$ is a hydrogen atom or a phenyl group or a phenyl group substituted by a fluorine, chlorine or bromine atom or a nitro, methyl or methoxyl group; $R_{25}$ is a hydrogen atom or a methyl group and $R_{26}$ is a lower alkyl, phenyl or lower alkoxy group or $R_{25}$ is joined to $R_{26}$ to form a phthalidyl group; and $R_{27}$ is a lower alkyl, phenyl, chlorophenyl or nitrophenyl group.

Favourably $R_{21}$ is a hydrogen atom or a methyl, ethyl or vinyl group. Favourably $R_{22}$ is a hydrogen atom. Favourably $R_{23}$ is a phenyl, p-bromophenyl, p-methoxyphenyl or p-nitrophenyl group. Favourably $R_{24}$ is a hydrogen atom. Favourably $R_{26}$ is a methyl, t-butyl or ethoxyl group or is joined to $R_{25}$. Favourably $R_{27}$ is a methyl group.

Particularly apt groups of the sub-formula (j) include the methyl and ethyl groups.

Particularly apt groups of the sub-formula (k) include the benzyl and p-nitrobenzyl groups.

Particularly apt groups of the sub-formula (l) include the acetoxymethyl, pivaloyloxymethyl, α-ethoxycarbonyloxyethyl and phthalidyl groups.

A preferred value for an esterifying radical is the p-nitrobenzyl group.

A preferred value for an esterifying radical is the phthalidyl group.

Thus one particularly apt group of compounds falling within formula (I) is that of the formula (III):

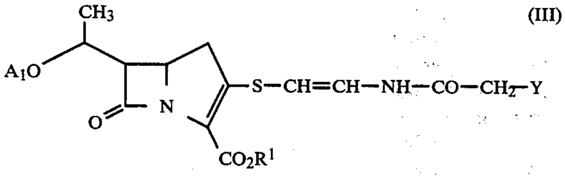
(III)

wherein Y and $R^1$ are as defined in relation to formula (I) and $A_1$ is a hydrogen atom or an acetyl group.

Aptly $CO_2R_1$ is a pharmaceutically acceptable salt of a carboxyl group when Y does not contain an amino or imino group.

Aptly $CO_2R_1$ is an in-vivo hydrolysable ester group such as the phthalidyl ester group.

Aptly $CO_2R_1$ is a p-nitrobenzyl ester group.

Particularly aptly Y contains an amino or imino group and a zwitterion is formed.

A favoured compound is that of formula (IV):

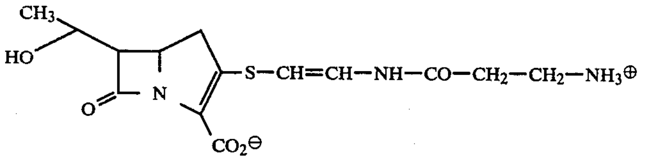
(IV)

A further favoured compound is that of the formula (V):

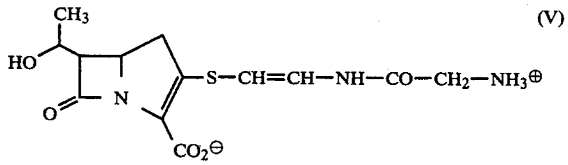
(V)

It will be realised that the compounds of the formulae (III)-(V) may exist in either of two epimeric forms at C-8 (8R or 8S); these epimers may be separated by conventional means such as fractional crystallisation, counter-current separation or chromatography. We have found that it is most convenient to separate the C-8 epimers by column chromatography.

The compounds of this invention, for example those of the formulae (I)-(V) are generally provided in the form of R,S-mixtures at C-5. It is believed that the active isomer from this mixture is that which exemplified in relation to formula (I) has the configuration shown in formula (VI):

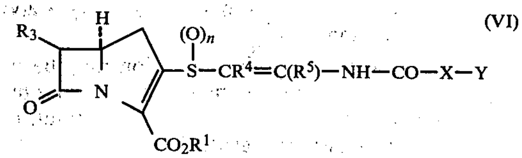
(VI)

The compounds of the formulae (I)-(VI) may have the R-, S- or mixtures of R- and S-configuration at C6. Thus using formula (VI) to demonstrate these configurations the compounds shown in formulae (VII) and (VIII) are worthy of note:

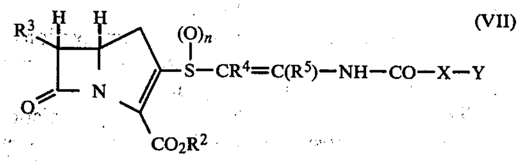
(VII)

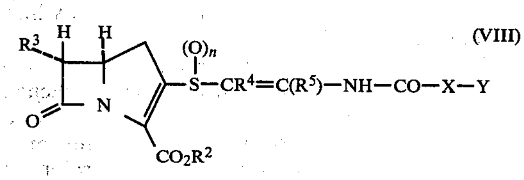
(VIII)

Pharmaceutically acceptable in-vivo hydrolysable esters are those esters which hydrolyse in the human body to produce the parent acid or its salt. Such esters may be identified by administration to a test animal such as a rat or mouse by intravenous administration and thereafter examining the test animal's body fluids for the presence of the compound of the formula (I) or its salt.

Suitable esters of this type include those of sub-formula (i) as hereinbefore defined.

In a further aspect of this invention there is provided a pharmaceutical composition which comprises a compound of the formula (I) or pharmaceutically acceptable salt or in-vivo hydrolysable ester thereof and a pharmaceutically acceptable carrier.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit-dose composition adapted for administration by injection.

Unit dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose fro a 70 kg adult is about 200 to 2000 mgs, for example about 400, 600, 750, 1000 or 1500 mgs.

The compositions of this invention may be used to treat bacterial infection, in mammals including humans, for example infections of the respiratory tract, urinary tract or soft tissues, or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato starch or polyvinylpolypyrrolidone, magnesium stearate or sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefore, suncillin, sulbenicillin, azlocillin or mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride and bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusion in the injectably administrable compositions of this invention include cephaloridine, cefazolin and cephradine, generally as their pharmaceutically acceptable salt.

The weight ratio between compound of this invention and penicillin or cephalosporin is generally from 10:1 to 1:10, more usually from 5:1 to 1:5 and normally from 3:1 to 1:3.

The penicillin or cephalosporin is generally utilised in its conventionally administered amount.

The compounds of the present invention may be prepared by reaction sequences such as those outlined in Schemes 1, 2 and 3. In the Schemes PNB means para-nitrobenzyl and SR means $SCR_4{=}C(R_5){-}NH{-}CO{-}X{-}Y$. Although Schemes 1 and 2 show the preparation of compounds with a 6-$CH(CH_3)OH$ group via compounds with a 6-$CH(CH_3)OCOPNB$ group it should be appreciated that other moieties $R_3$ may be included at the 6-position, e.g. one of the sub-formulae (i), (j), (k) or (l) as hereinbefore defined.

SCHEME 1

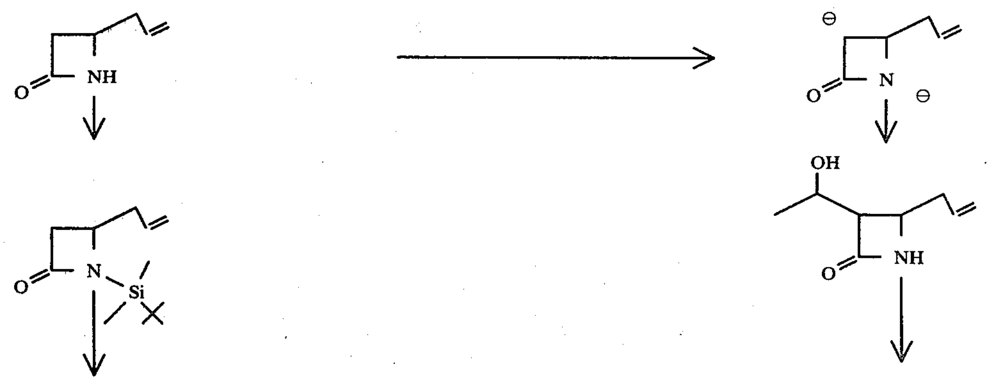

-continued
SCHEME 1
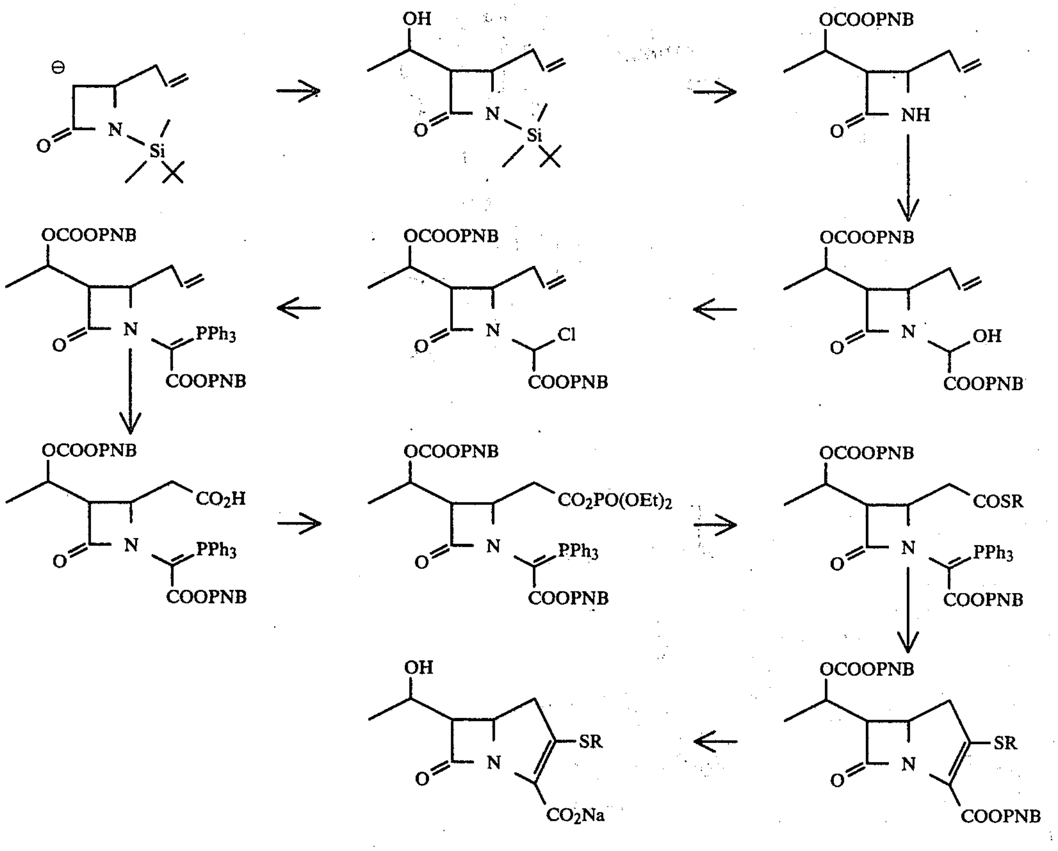
SCHEME 2
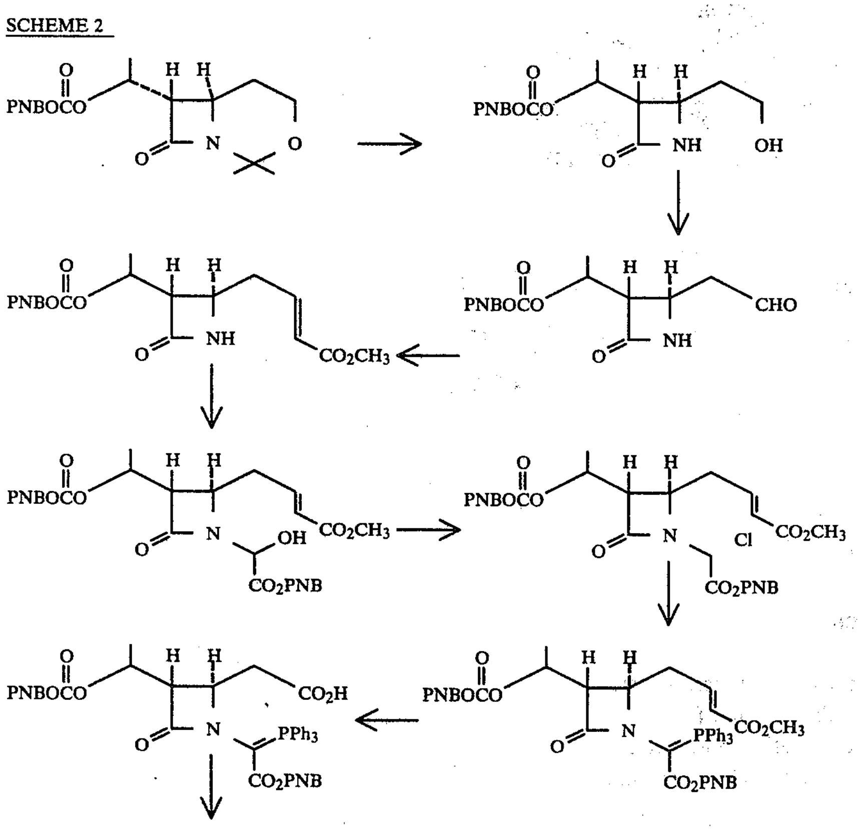

-continued
SCHEME 2
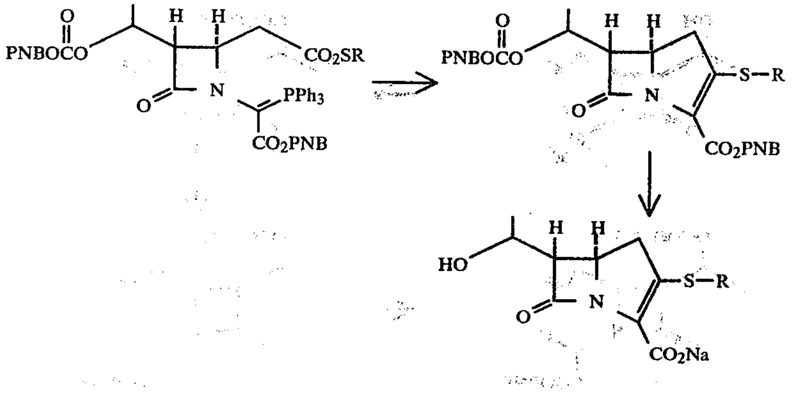
SCHEME 3
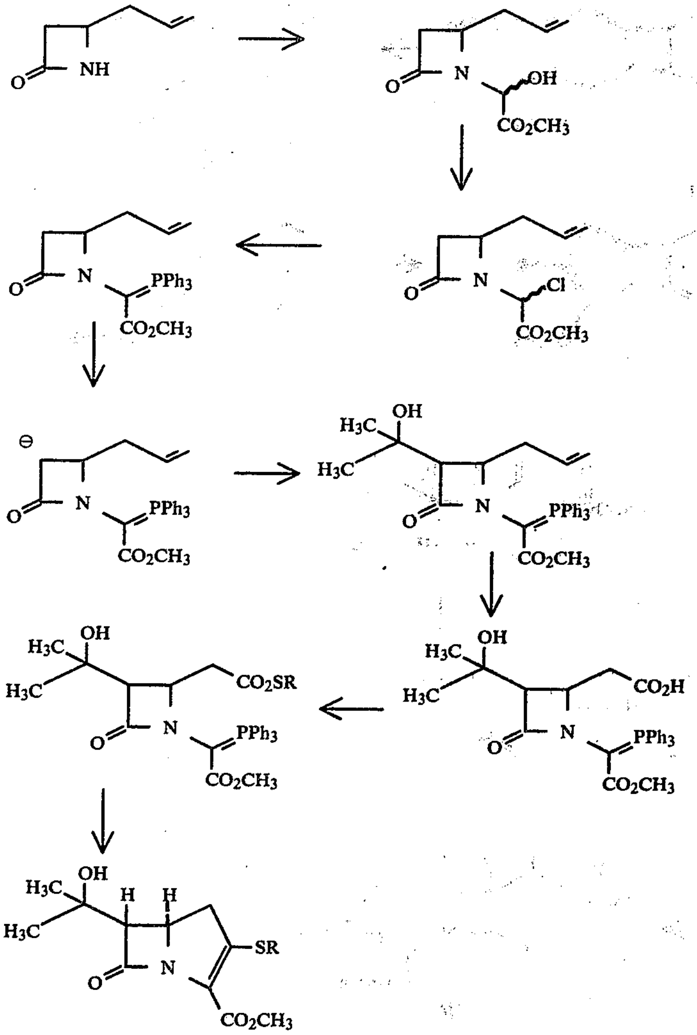
The present invention also proves a process for the preparation of a compound of the formula (I) which process comprises the ring closing elimination of the elements of $O{=}PA_2A_3A_4$ from an ester of a compound of the formula (IX):

(IX)

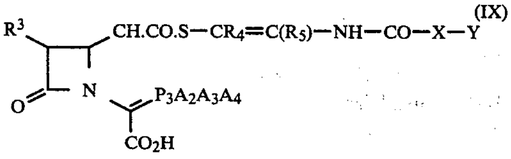

wherein $A_2$, $A_3$ and $A_4$ are independently phenyl or methoxyphenyl, and $R^3$, $R_4$, $R_5$, X and Y are as defined in relation to formula (II); and thereafter if necessary performing one or more of the following steps:

(i) converting any ester that is not in-vivo hydrolysable into an acid, pharmaceutically acceptable salt or in-vivo hydrolysable ester, (ii) converting any ester that is in-vivo hydrolysable into an acid, pharmaceutically acceptable salt or different in-vivo hydrolysable ester, (iii) oxidising the C-3 thio substituent to form a sulphoxide, (iv) sulphonating a hydroxy group to form a sulphate group.

Preferably $A_2$, $A_3$ and $A_4$ are each phenyl.

Any reactive moiety present in $R^3$, X or Y may be protected during the ring closure if desired, for example as p-nitrobenzyloxycarbonyl derivative.

The ring closure is normally brought about by heating the ester of the compound of the formula (IX) in an inert solvent; for example temperatures of 90°-120° C. and more suitably 100°-110° C. may be employed in a solvent such as toluene or the like. The reaction is best carried out under dry conditions under an inert gas.

Oxidation of the C-3 thio substituent may be performed in conventional manner, for example using a perbenzoic acid in dichloromethane. Sulphonation of a hydroxy group may be performed in conventional manner for example using pyridine sulphuric anhydride in pyridine.

The ester of the compound (I) produced may be isolated by any standard method such as fractional crystallisation, counter current separation or chromatography. We have found that it is most convenient to separate the desired product by column chromatography.

Any convenient ester may be used in the process of this invention. Since it is frequently desirable to form a zwitterion or salt of compounds (I), the ester employed is preferably one which is readily converted to the parent acid or its salt by mild methods of hydrogenolysis. In a further aspect therefore the invention includes a process for preparing a salt or free acid of a compound (I) which process comprises de-esterifying an ester of a compound of formula (I). Particularly suitable esters for use in this process include benzyl esters, optionally substituted in the para position by a lower alkoxy, or nitro group or a halogen atom.

A preferred ester for use in this process is the p-nitrobenzyl ester.

Esters of compounds (I) may be de-esterified by conventional methods of hydrogenolysis.

If a compound of the formula (I) contains two ester groups then it is preferable that at least one ester group is readily convertible to the parent acid or its salt by mild methods of hydrogenolysis.

Suitable methods include hydrogenation in the presence of a transition metal catalyst. The pressure of hydrogen used in the reaction may be low, medium or high but in general an approximately atmospheric or slightly super-atmospheric pressure of hydrogen is preferred. The transition metal catalyst employed is preferably palladium on charcoal or on calcium carbonate. The hydrogenation may be effected in any inert solvent in which the ester is soluble such as aqueous dioxan or the like. If this hydrogenation is carried out in the presence of a base then a salt of compound (I) is produced. Suitable bases for inclusion include $NaHCO_3$, $KHCO_3$, $NaCO_3$, $K_2CO_3$, $CaCO_3$, $MgCO_3$, $LiHCO_3$, $NH_4OCOCH_3$ and the like. If no base is present then hydrogenation leads to the preparation of an acid within formula (II) which may then be neutralised if desired to yield a salt. Suitable bases which may be used to neutralise acids within formula (I) include LiOH, NaOH, $NaHCO_3$, KOH, $Ca(OH)_2$ and $Ba(OH)_2$.

The salts of acids (I) may be converted to esters in conventional manner, for example by reaction with a reactive halide such as bromophthalide in solution in dimethylformamide or like solvent.

The substituent group or groups within the groups $R_3$*, X and Y in the compounds of formula (I) may be varied by conventional reactions. Thus for example when a substitute comprises a nitro group this may be reduced in a conventional manner to an amino group, for example by catalysed hydrogenation. Similarly an amino group may be acylated to give a substituted amino group, for example by treatment with an acyl halide in the presence of an organic base. Substituents such as $NHCO_2$p-nitrobenzyl or $OCO_2$p-nitrobenzyl may be converted to an amino or hydroxyl group for example by hydrogenolysis.

Compounds of the formula (I) wherein Y is a group $N{=}C(R_{14}){-}NHR_{15}$ are most conveniently prepared by the reaction of compound of the formula (II) wherein Y is a $-NH_2$ group with an imido ester $R_{14}{-}C(OR'){=}NR_{15}$ wherein $R_{14}$ and $R_{15}$ are as defined in relation to a compound of the formula (I) and OR' is a leaving group wherein $R^1$ is a $C_{1-6}$ alkyl group, preferably $C_{1-3}$ alkyl such as methyl or ethyl. This reaction may be most conveniently performed at ambient temperature in water, dioxan, tetrahydrofuran, dimethylformamide, acetone or mixtures thereof.

Compounds of the formula (I) wherein Y is a group $N{=}C(R_{14}){-}NR_{15}R_{16}$ may be most conveniently prepared by the reaction of a compound of the formula (II) wherein Y is a $-NH_2$ group with an imino halide $[R_{14}{-}C(X'){=}NR_{15}R_{16}]^{\oplus}X'^{\ominus}$ wherein $R_{14}$, $R_{15}$ and $R_{16}$ are as defined in relation to a compound of the formula (I) and X' is a halogen atom for example a chlorine atom. This reaction may be most conveniently performed at ambient temperature in water, dioxan, tetrahydrofuran, dimethylformamide acetone or mixtures thereof; and is preferably followed by mild acidic hydrolysis to provide the zwitterion of the compound of the formula (I).

The ester of the compound of the formula (IX) may be prepared by the reaction of a corresponding ester of a compound of the formula (X):

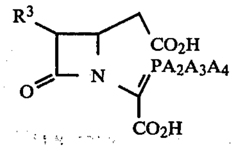

(X)

wherein $R^3$ $A_2$, $A_3$ and $A_4$ are as defined in relation to formula (II) with a diloweralkylphosphorochloridate or thionylchloride and a triloweralkylamine followed by reaction with a derivative of the formula (XI):

$L^{\oplus}{}^{\ominus}S—CR_4=C(R_5)—NH—CO—X—Y$ (XI)

wherein $L^{\oplus}$ is a sodium, silver or thallium I cation or an ammonium ion substituted by up to three lower alkyl groups, and $R_4$, $R_5$, X and Y are as defined in relation to formula (II). $L^{\oplus}$ may also be a lithium cation.

When $L^{\oplus}$ is a substituted ammonium ion, it is preferably a tertiary ammonium ion, such as the tri-ethylammonium ion. It is conveniently generated in situ by the reaction of a compound of the formula $HSCR_4=C(R_5)—NH—CO—X—Y$ with an amine, preferably a tertiary amine.

Preferably $L^{\oplus}$ is a thallium I cation or a silver cation.

A particularly suitable diloweralkylphosphorochloridate is diethylphosphorochloridate.

A particularly suitable triloweralkylamine is triethylamine.

The reaction is generally carried out in an inert organic solvent such as tetrahydrofuran at a non-extreme temperature such as 0° to 40° C., for example 15°-25° C.

The compound of the formula $HSCR_4=C(R_5)—NH—CO—X—Y$ may be prepared by the reaction of $NH_2CO—X—Y$ (in which Y is suitably protected by means of a standard peptide protecting group such that for example Y is p-nitrobenzyloxycarbonylamino) with $Ph_3C—S—CHR_4—CR_5(OEt)_2$ or a similar reagent; and thereafter cleaving the trityl group. For further information on the preparation of such compounds see European Patent Application Publication No. 003740 wherein analogous methods are disclosed.

The ester of the compound of the formula (X) may be prepared by the reaction of an ester of the compound of the formula (XII):

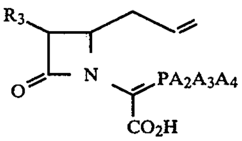

(XII)

wherein $R_3$ $A_2$, $A_3$ and $A_4$ are as defined as in relation to formula (II) with ozone in the presence of trifluoroacetic acid followed by m-chloroperbenzoic acid.

The ozonolysis is generally performed at a depressed temperature such as −40° to −80° C., for example about −70° C. and in solution in an inert solvent such as methylene chloride. Excess ozone is removed by flushing with an inert gas and thereafter a solution of the peracid is added to the reaction mixture.

The ester of the compound of the formula (XII) may be prepared from the corresponding ester of a compound of the formula (XIII):

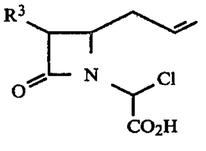

(XIII)

wherein $R^3$ is as defined in relation to formula (III) with $PA_2A_3A_4$ wherein $A_2$, $A_3$ and $A_4$ are as hereinbefore defined.

This reaction is normally effected in the presence of at least one equivalent of a base of relatively low nucleophilicity such as 2,6-lutidine at an ambient temperature in a dry solvent such as dioxan, tetrahydrofuran or the like.

The ester of the compound of the formula (XIII) may be prepared from the corresponding ester of the carbinol of the formula (XIV):

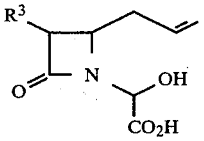

(XIV)

wherein $R^3$ is as defined in relation to formula (III) by reaction with thionyl chloride.

This reaction is also normally effected in the presence of at least one equivalent of a base of relatively low nucleophilicity in a dry solvent such as dioxan or tetrahydrofuran but in this instance the reaction is performed at a depressed temperature, for example −30° to −10° C.

The preceding carbinol may be prepared by the reaction of a compound of the formula (XV):

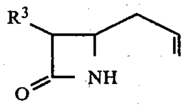

(XV)

wherein $R^3$ is as defined in relation to formula (III) with a glyoxylic acid ester.

Normally this reaction is carried out in an inert solvent at an elevated temperature, for example in dry benzene under reflux.

The esters of the compounds of the formula (XIV) may also be prepared by esterification of a salt of the compound of the formula (XIV) in conventional manner. Suitable methods include the reaction of alkali metal salt such as a sodium or potassium salt with a reactive halide or sulphonate ester such as a bromide, chloride, mesylate, tosylate or the like. Such esterifications may be carried out under conventional conditions, for example in dimethylformamide at room temperature.

The salt of compound of the formula (XIV) may be prepared by neutralisation of the acid of the formula (XIV), for example with an alkali metal carbonate or bicarbonate, for example sodium or potassium carbonate.

The compound of formula (XIV) may be prepared by the reaction of glyoxlic acid with the compounds of the formula (XV) as hereinbefore defined.

The compounds of the formula (XV) wherein $R_3$ is not a hydrogen atom may be prepared by the reaction of the compound of the formulae (XVa) or (XVb):

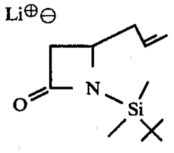

(XVa)

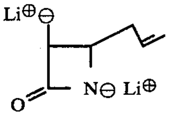

(XVb)

with a compound of the formula (XVI) or (XVII):

$R_{11}.CO.R_{12}$ (XVI)

$R_{11}(R_{12})CHX$ (XVII)

wherein $R_{11}$ and $R_{12}$ are as defined in relation to formula (II) and X is a chlorine, bromine or iodine atom; and thereafter acylating the product formed by reaction with the compound of the formula (XIV) if desired.

Generally the compound of the formula (XVb) is generated and utilized in situ. Thus 4-allyl-azetidin-2-one may be treated with two equivalents of n-butyl lithium in tetrahydrofuran at a low temperature. The dianion may be quenched by the addition of a compound of the formula (XVI) or (XVII).

The compound of the formula (XV) wherein $R_3$ is not a hydrogen atom also may be prepared by the reaction of the compound of the formula (XVa):

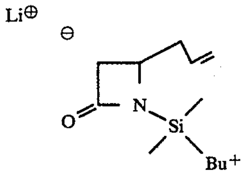
(XVa)

with a compound of the formula (XVI) or (XVII) as hereinbefore defined.

Generally the compound of the formula (XVa) is generated and utilised in situ. Thus 4-allyl-1-t-butyldimethylsilylazetidin-2-one may be treated with two equivalents of n-butyl lithium in tetrahydrofuran at a low temperature. The anion may be quenched by the addition of a compound of the formula (XVI) or (XVII). 4-Allyl-1-t-butyldimethysilylazetidin-2-one with t-butyldimethylsilyl chloride and triethylamine in an inert solvent. The t-butyldimethylsilyl protecting group may be removed, when necessary, on treatment with potassium fluoride and a crown ether in an inert solvent.

The esters of the compound of the formula (X) may also be prepared by the ozonolysis of an ester of a compound of the formula (XVIII):

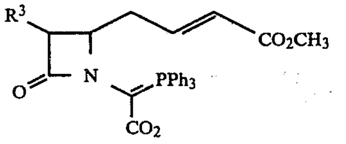
(XVIII)

wherein $R^3$ is as defined in relation to formula (I) followed by m-chloroperbenzoic acid.

The ozonolysis is generally performed in the presence of trifluoroacetic acid in methylene chloride at −70° C.

The ester of the compound of the formula (XVIII) may be prepared via reaction of triphenylphosphine and the corresponding chloro compound which may in turn be prepared from the corresponding hydroxy compound which may be prepared from the N-H compound of the formula (XIX):

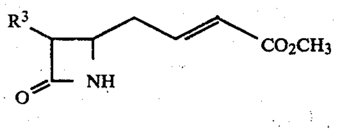
(XIX)

wherein $R^3$ is as defined in relation to formula (I). This sequence may be carried out in analogous manner to the sequence (XIV)→(XIII)→(XII) as hereinbefore described.

The compound of the formula (XIX) may be prepared by the oxidation of a compound of the formula (XX):

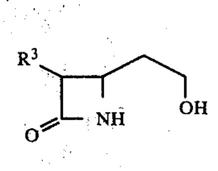
(XX)

wherein $R^3$ is as defined in relation to formula (I) with pyridinium chlorochromate and thereafter reacting in situ the thus produced aldehyde of the formula (XXI):

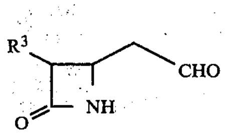
(XXI)

with $Ph_3P{=}CHCO_2CH_3$.

The oxidation may be carried out in methylene chloride or the like at room temperature. When the oxidation is judged complete (for example by tlc) the reaction may be filtered and the phosphorane may be added to the filtrate for reaction.

The compound of the formula (XX) may be prepared by the mild acid hydrolysis of a corresponding compound of the formula (XXII):

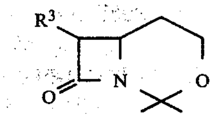
(XXII)

or the corresponding spirocyclohexyl analogue wherein $R_3$ is as defined in relation to formula (I)

The preceding hydrolysis may be carried out in aqueous acetone using small quantities of mineral acid for example sulphuric acid.

Esters of the compound of the formula (XII) may also be prepared by the reaction of an ester of a compound of the formula (XXIII):

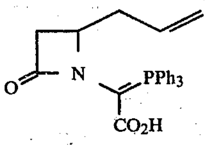
(XXIII)

with a compound of the formula (XVI) or (XVII) as hereinbefore defined in the presence of a strong base and thereafter if desired acylating the product formed by reaction with a compound of the formula (XVI).

Strong bases for use in this reaction are those of low nucleophilicity such as lithium N,N-isopropylcyclohexylamide and similar reagents. The reaction is generally carried out in tetrahydrofuran at a low temperature such as −80° C.

The compound of the formula (XIV) may be prepared from the corresponding chloro compound which in turn may be prepared from the corresponding N-H compound by processes analogous to that for the sequence (XV)-(XIV) (XIII) as hereinbefore described.

Isomerisation of terminal moieties of sub-formula (e) may be effected using a mercuric salt in the presence of an inert solvent. The presence of a buffering agent to control the pH of this isomerisation reaction has proved advantageous. A suitable agent for this purpose is calcium carbonate.

Preferably this isomerisation reaction is carried out on a compound of the formula (I) wherein $R_1$ is an esterifying group, since separation of the geometric isomer of the formula (I) from other materials may then generally be achieved more easily than when the compounds contain a free or salted acid group.

The solvent used in the process will be selected primarily on the basis of the solubility of the compound (I) therein, a large number of solvents being suitable; for example, acetonitrile, acetone, dichloromethane, chloroform and water. A suitable solvent mixture is acetonitrile-water.

The reaction is generally carried out at a moderate temperature, for example, from −30° to +50° C., room temperature being particularly convenient, when the reaction is generally complete in a few minutes.

We have found in general that when $R^4$ and $R^5$ are hydrogen atoms the cis-configuration of the double bond is preferred as such compounds tend to have superior efficacy, for example antibacterial activity and/or stability, with regard to the corresponding trans compounds.

European Patent Application Publication No. 0000828 should be consulted for descriptions of the preparation of intermediates. European Patent Application Nos. 0001627 and 0001628 may also be referred to. Other helpful disclosures include French Patent Application Publication Nos. 2392996 and 2371449. Further procedures for the preparation of intermediates are found in European Patent Application Publication No. 0003240 and U.S. Ser. No. 004,896.

EXAMPLE 1

5(R,S), 6(S,R) 3-(Z)-2-Glycinamidoethenylthio-6-(1R-hydroxyethyl)-7-oxo-1-azabicyclo[3.2.0]hept-2-ene-2-carboxylate

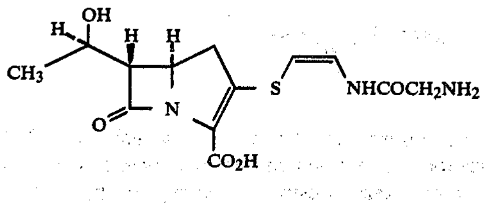

(i) Preparation of t-Butoxycarbonylglycine-m-nitrophenyl ester

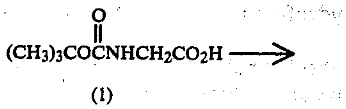

(1)

-continued

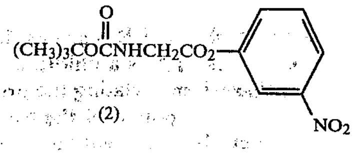

(2)

t-Butoxycarbonylglycine (8.7 g) was dissolved in methylene chloride (25 ml), m-nitrophenyl (7.5 g) added at 0° followed by DCCI (11.9 g) and the mixture stirred at room temperature overnight. The solution was filtered and washed with 20% citric acid (25 ml) and dilute sodium bicarbonate solution (3×20 ml). The organic phase was dried ($MgSO_4$) and the solvent evaporated to give the product (2) from ethyl acetate/petrol (60°–80°) m.p. 77°–8° (13 g; 88%) $\nu_{max}$ ($CHCl_3$) 3300, 1790, 1710, 1680, 1530, 1470 $cm^{-1}$.

(ii) Preparation of Glycine m-nitrophenyl ester.p-tosylate

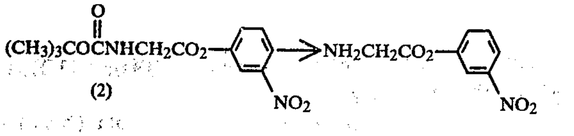

(2)

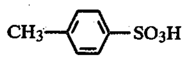

(3)

The ester (2) (9.9 g) was dissolved in trifluoroacetic acid (10 ml) containing toluene-p-sulphonic acid monohydrate (6.3 g) and stirred at room temperature for ½ hour. Ethyl acetate (100 ml) was added and the product (3) was collected, washed well with ethyl acetate and dried (7 g; 57%) m.p. 198°–201° $\nu_{max}$ ($CHCl_3$) 3100, 1775, 1525, 1460, 1375, 1345 $cm^{-1}$.

(iii) Preparation of p-Nitrobenzyloxycarbonylglycine-m-nitrophenyl ester

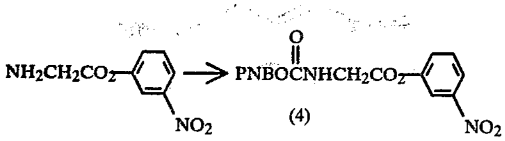

(4)

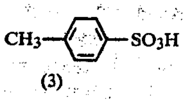

(3)

The tosylate salt (3) (7.4 g) was dissolved in methylene chloride (25 ml) and treated with triethylamine (2.2 g). The mixture was cooled to −20° and p-nitrobenzylchloroformate (4.5 g) was added. The mixture was stirred at −20° for half and hour and allowed to warm to 0°. The solution was washed with 20% citric acid (25 ml) and saturated sodium bicarbonate solution (3×25 ml) and dried ($MgSO_4$). Evaporation of the solvent and chromatography of the residue on Merck Keiselgel 60 (<230 mesh) gave the product (4) as a colourless solid from ethyl acetate (8 g; 93%) m.p. 115°–6°. $\sigma_{max}$ (Nujol) 3100, 1775, 1525, 1460, 1375, 1345 $cm^{-1}$.

(iv) Preparation of p-Nitrobenzyloxycarbonylglycinamide

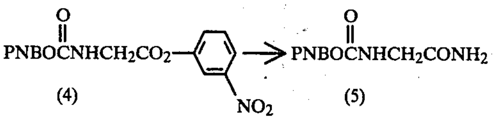

(4) (5)

The ester (4) (7.5 g) was dissolved in methylene chloride (125 ml) and ammonia was bubbled into the solution for ½ hour at room temperature. The reaction was left at room temperature for a further hour. The precipitated amide (5) was filtered off and collected as a white solid m.p. 192°-3° (3.5 g; 70%) $\nu_{max}$ ($CHCl_3$) 3450, 3300, 3150, 1705, 1675, 1605, 1545, 1510, 1460, 1345 $cm^{-1}$. δ ppm [$(CD_3)_2SO$] 3.57 (2H, d, J 6.5 Hz, $CH_2$) 5.17 (2H, s, $C\underline{H}_2Ar$) 6.98 and 7.39 (3H, br signals [exchangeable] NH and $CONH_2$) 7.61 and 8.20 (4H, ABq, J 9 Hz, Ar's).

(v) Preparation of (Z)- and (E)-2-p-Nitrobenzyloxycarbonylglycinamido-1-triphenylmethylthioethene

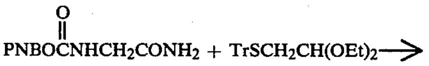

(5) (6)

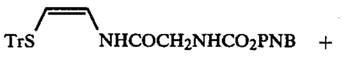

(7)

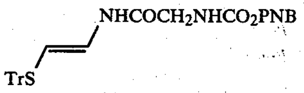

(8)

The amide (5) (2.5 g) was dissolved in dimethylformamide (30 ml) and treated with tritylthioethyldiethylacetal (6) (3.9 g) followed by toluene-p-sulphonic acid monohydrate (1.95 g). The reaction was stirred at 90° for two hours. The solvent was evaporated and the residue chromatographed on Merck keiselgel 60 (<230 mesh) eluting with petrol (60°-80°)/ethyl acetate to yield a mixture of isomers (7) and (8), complete separation of which was accomplished by repeat chromatography. Thus the (Z)-isomer (7) was isolated as a colourless solid from ethyl acetate/petrol (60°-80°) m.p. 79°-80° (0.6 g; 11%) $\nu_{max}$ ($CHCl_3$) 3430, 3380, 1730, 1700, 1625, 1525, 1475 and 1350 $cm^{-1}$. δ ppm [$(CD_3)_2SO$] 3.78 (2H, d, J 6,5 Hz, $CH_2$) 4.80 (1H, d, J 8 Hz, $C\underline{H}$-S) 5.16 (2H, s, $C\underline{H}_2Ar$) 6.72 (1H, dd, J 11, 8 Hz, $C\underline{H}$-N) 7.25 (15H, s, Tr) 7.56 and 8.18 (4H, ABq, J 8.5 Hz, Ar's) 9.41 (1H, d, J 11 Hz, NH) (Found: C, 65.43; H, 5.05; N, 6.66, $C_{31}H_{27}N_3O_5S$. $H_2O$ requires C, 65.14; 5.08; N, 7.35).

The (E)-isomer (8) crystallised from ethyl acetate as a colourless solid m.p. 170°-1° (0.5 g; 10%) $\nu_{max}$ (Nujol) 3450, 3330, 3280, 1720, 1675, 1610, 1510, 1460 $cm^{-1}$. δ ppm ($[CD_3]_2SO$) 3.58 (2H, d, J 6.5 Hz, $CH_2$) 5.18 (2H, s, $C\underline{H}_2Ar$) 5.38 (1H, d, J 16 Hz, $=C\underline{H}-S$) 6.89 (1H, m, collapses to d, J 16 Hz, on $D_2O$ exchange, $CH=\underline{N}H-$) 7.26 (15 H, s, Tr) 7.59 and 8.22 (4H, ABq, J 8.5 Hz, Ar's), 10.07 (1H, d, J 9.5 Hz, NH). One NH obscured by aromatic protons.

(vi) Preparation of Silver(Z)-2-p-Nitrobenzyloxycarbonylglycinamido-1-ethenylthiolate

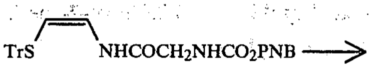

(7)

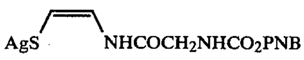

(9)

The sulphide (7) (0.55 g) was dissolved in methanol (25 ml) and finely-ground silver nitrate (0.17 g) in methanol (5 ml) was added with pyridine (0.08 g). The mixture was stirred at room temperature for three hours and the yellow silver salt (9) collected by centrifugation. The collected salt was washed twice with methanol and twice with ether and dried. (0.37 g; 90%) $\nu_{max}$ (Nujol)3300, 1700, 1630, 1605, 1520, 1465, 1350 $cm^{-1}$.

(vii) Preparation of 3(R,S), 4(S,R) 4-(Z)-2-p-Nitrobenzyloxycarbonylglycinamidoethenylthiocarbonylmethyl-3-3-(1R-p-nitrobenzyloxycarbonyloxyethyl)-1-(1R-p-nitrobenzyloxycarbonyl-1-triphenylphosphoranylidene methyl)azetidin-2-one

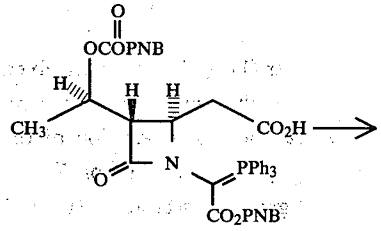

(10)

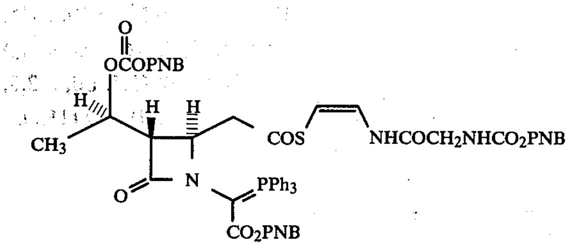

(11)

3(R,S),4(S,R)-4-Carboxymethyl-3-(1R-p-nitrobenzyloxycarbonyloxyethyl)-1-(1-p-nitrobenzyloxycarbonyl-1-triphenylphosphoranylidenemethyl)azetidin-2-one (10) (0.4 g) was dissolved in dry acetonitrile (5 ml) containing dimethylformamide (3 drops). Thionyl chloride (0.06 g) in dry acetonitrile was added dropwise and stirred at room temperature for two hours. Pyridine (0.04 g) was added followed by silver(Z)-2-p-nitrobenzyloxycarbonylglycinamido-1-ethenylthiolate (0.26 g; 1.25 equivs.). The reaction was stirred at room temperature for one hour, filtered and the solvent evaporated. Chromatography of the residue on Merck Keiselgel 60 (<230 mesh) gave the phosphorane thioester (11) as a gum $\nu_{max}$ ($CHCl_3$) 3400, 1740, 1705, 1635, 1605, 1525, 1345 $cm^{-1}$.

(viii) Preparation of 5(R,S), 6(S,R) p-Nitrobenzyl-3-(Z)-2-p-Nitrobenzyloxycarbonylglycinamidoethenylthio-1-(1R-p-nitrobenzyloxycarbonyloxyethyl)-7-oxo-1-azabicyclo[3.2.0]hept-2-ene-2-carboxylate

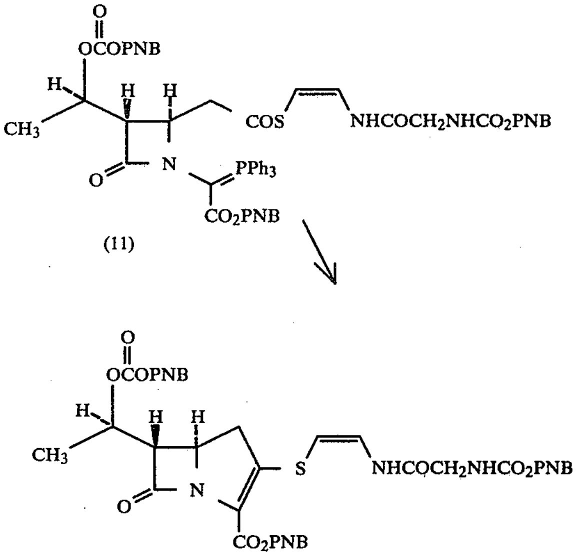
(11)

(12)

The phosphorane thioester (11) (0.2 g) was dissolved in dry toluene (filtered through basic alumina) and refluxed under argon for 22 hours. Evaporation of the solvent and chromatography of the residue on Merck Keiselgel 60 (<230 mesh) gave the product (12) (0.012 g; 8%) as a gum $\nu_{max}$ (EtOH) 323, nm, 265 nm. $\nu_{max}$ ($CHCl_3$) 3450, 3400, 1785, 1749, 1710, 1635, 1610, 1525, 1350 $cm^{-1}$. δ ppm ($CDCl_3$) 1.48 (3H, d, J 6.5 Hz, $CH_3$) 3.10 (2H, dd, J 4.5, 9 Hz, C4-$CH_2$) 3.42 (1H, dd, J 2.5, 7.5 Hz, C6-H) 3.98 (2H, d, J 6 Hz, $CH_2NH$) 4.12 (1H, m, C5-H) 5.10 to 5.60 (8H, complex pattern, S—C<u>H</u>=, $CH_2Ar$'s, C<u>H</u>O) 7.55 and 8.27 (18H, complex pattern, $CH_2Ar$'s, =C<u>H</u>—NHCO and NH's).

(ix) Preparation of 5(R,S), 6(S,R) 3-(Z)-2-glycinamidoethenylthio-6-(1R-hydroxyethyl)-7-oxo-1-azabicyclo[3.2.0]hept-2-ene-2-carboxylate

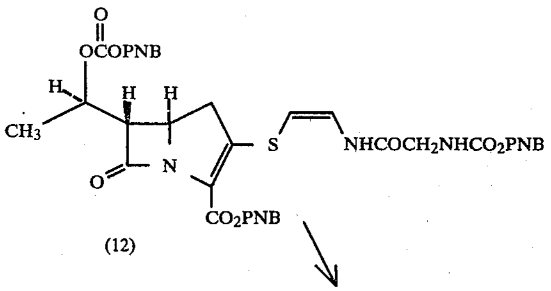
(12)

-continued

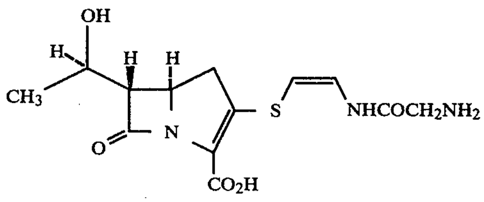
(13)

The bicyclic azetidinone (12) (0.008 g) was dissolved in dioxan (5 ml) containing ethanol (0.2 ml), water (0.5 ml) and $^{M}/20$ phosphate buffer (0.7 ml) 10% Pd/C (0.015 g) was added and the solution hydrogenated for three hours at ambient temperature and pressure. The solution was filtered through Kieselguhr and washed with ether (3×10 ml). The aqueous phase contained the product (13) (0.0006 g) $\lambda_{max}$ 237, 306 nm.

The concentrations of this compound required to inhibit the growth of the following bacteria are given below:

| Organism | μg/ml$^{-1}$ (microtitre in broth) |
|---|---|
| *Citrobacter freundii* E8 | 0.8 |
| *Enterobacter cloacae* N1 | 1.6 |
| *Escherichia coli* 0111 | 0.2 |
| *Escherichia coli* JT39 | 0.4 |
| *Klebsiella aerogenes* A | 0.8 |
| *Proteus mirabilis* C977 | 1.6 |
| *Proteus morganii* 1580 | 0.8 |
| *Proteus rettgeri* WM16 | 1.6 |
| *Proteus vulgaris* WO91 | 0.8 |
| *Pseudomonas aeruginosa* A | 50.0 |
| *Salmonella typhimurium* CT10 | 0.8 |
| *Serratia marcescens* US20 | 0.8 |
| *Shigella sonnei* MB 11967 | 1.6 |
| *Staphylococcus aureus* Oxford | 0.1 |
| *Staphylococcus aureus* Russell | 0.4 |
| *Staphylococcus aureus* 1517 | 0.4 |
| *Streptococcus faecalis* 1 | 0.8 |
| *Streptococcus pneumoniae* CN33 | ≦0.1 |
| *Streptococcus pyogenes* CN10 | ≦0.1 |
| *E. coli* ESS | 0.2 |

EXAMPLE 2

5(R,S), 6(S,R) 3-(E)-2-Glycinamidoethenylthio-6-(1R,S-hydroxyethyl)-7-oxo-1-azabicyclo[3.2.0]hept-2-ene-2-carboxylate

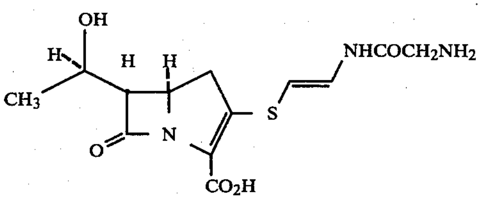

(i) Preparation of 5(R,S), 6(S,R) p-Nitrobenzyl-3-(E)-2-p-Nitrobenzyloxycarbonyl-glycinamidoethenylthio-1-(1R,S-p-nitrobenzyloxycarbonyloxyethyl)-7-oxo-1-azabicyclo[3.2.0]hept-2-ene-2-carboxylate

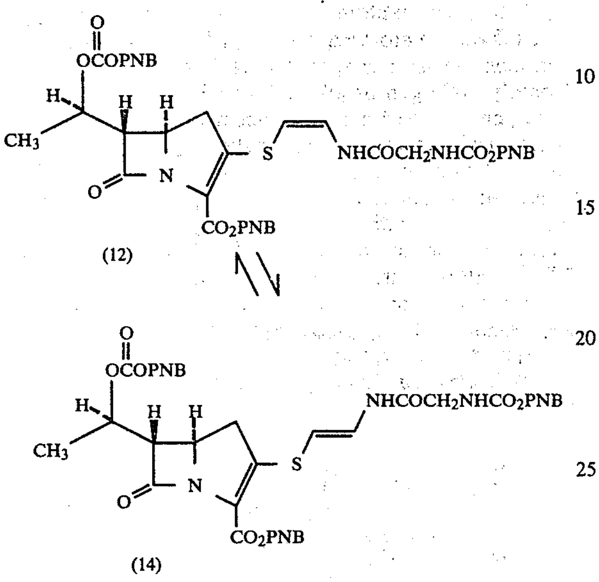

(12)

(14)

The bicyclic azetidinone (12) (0.05 g) was dissolved in 25% aqueous acetonitrile (8 ml) and treated with mercuric chloride (0.016 g). The reaction was stirred at room temperature for ten minutes and extracted with ethyl acetate (25 ml), washed with dilute sodium bicarbonate solution (3×10 ml) and dried ($MgSO_4$). Evaporation of the solvent and chromatography on Merck Keiselgel 60 (<230 mesh) gave the product (14) (0.02 g; 40%) as a viscous gum $\lambda_{max}$ (EtOH) 325, 266 nm. $\nu_{max}$ (nujol) 3420, 3300, 1800, 1735, 1700, 1640, 1615, 1525 $cm^{-1}$.

(ii) Preparation of 5(R,S), 6(S,R) 3-(E)-2-glycinamido-ethenylthio-6-(1RS-hydroxyethyl)-7-oxo-1-azabicyclo[3.2.0]hept-2-ene-2-carboxylate

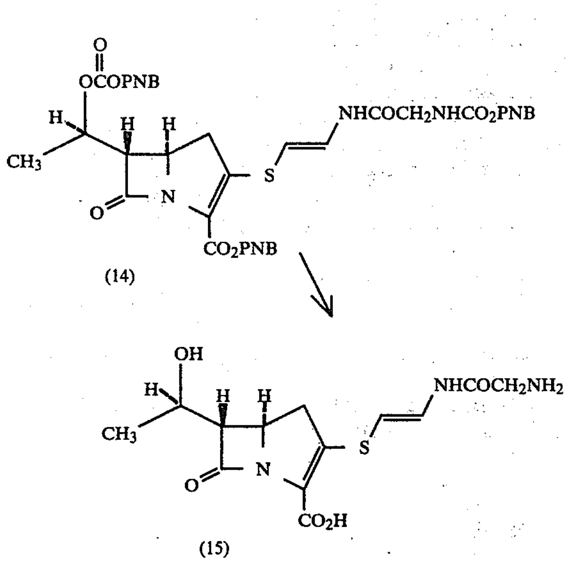

(14)

(15)

The bicyclic azetidinone (14) (0.012 g) was dissolved in dioxan (1.5 ml) containing water (1 ml) and M/20 phosphate buffer (1.4 ml). 10% Pd/C (0.02 g) was added and the solution hydrogenated for 2½ hours at ambient temperature and pressure. The solution was filtered through Kieselguhr and washed with ether (3×10 ml). The aqueous phase contained the product (15) 0.0015 g $\lambda_{max}$ ($H_2O$) 233, 308 nm.

The concentrations of this compound required to inhibit the growth of the following bacteria are given below:

| Organism | $\mu g/ml^{-1}$ (microtitre in broth) |
|---|---|
| *Citrobacter freundii* E8 | 1.6 |
| *Enterobacter cloacae* N1 | 1.6 |
| *Escherichia coli* 0111 | 0.4 |
| *Escherichia coli* JT39 | 0.4 |
| *Klebsiella aerogenes* A | 0.8 |
| *Proteus mirabilis* C977 | 3.1 |
| *Proteus morganii* 1580 | 3.1 |
| *Proteus rettgeri* WM16 | 1.6 |
| *Proteus vulgaris* WO91 | 1.6 |
| *Pseudomonas aeruginosa* A | 50 |
| *Salmonella typhimurium* CT10 | 1.6 |
| *Serratia marcescens* US20 | 1.6 |
| *Shigella sonnei* MB 11967 | 0.8 |
| *Bacillus subtilis* A | 0.2 |
| *Staphylococcus aureus* Oxford | ≦0.1 |
| *Staphylococcus aureus* Russell | 0.2 |
| *Staphylococcus aureus* 1517 | 6.2 |
| *Streptococcus faecalis* 1 | 1.6 |
| *Streptococcus pneumoniae* CN33 | 0.2 |
| *Streptococcus pyogenes* CN10 | 0.2 |
| *E. coli* ESS | 0.4 |

EXAMPLE 3

5(R,S), 6(S,R) 3-(Z)-2-Aminoethylamido-ethenylthio-6-(1R,S-hydroxyethyl)-7-oxo-1-azabicyclo[3.2.0]hept-2-ene-2-carboxylate

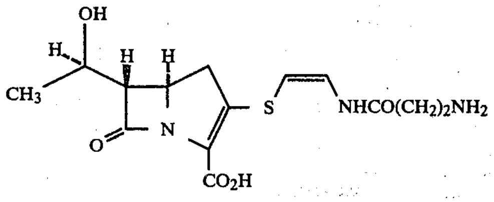

The title compound was prepared in an identical way to that described for Example I. The product was obtained in aqueous solution $\lambda_{max}$ ($H_2O$) 238, 305 nm.

The concentrations of this compound required to inhibit the growth of the following bacteria are given below.

| Organism | $\mu g/ml^{-1}$ (microtitre in broth) |
|---|---|
| *Citrobacter freundii* E8 | 1.6 |
| *Enterobacter cloacae* N1 | 3.1 |
| *Escherichia coli* 0111 | 0.8 |
| *Escherichia coli* JT39 | 0.8 |
| *Klebsiella aerogenes* A | ≦0.1 |
| *Proteus mirabilis* C977 | 6.2 |
| *Proteus morganii* 1580 | 1.6 |
| *Proteus rettgeri* WM16 | 3.1 |
| *Proteus vulgaris* WO91 | 3.1 |
| *Pseudomonas aeruginosa* A | 100 |
| *Salmonella typhimurium* CT10 | 3.1 |
| *Serratia marcescens* US20 | 0.8 |
| *Shigella sonnei* MB 11967 | 0.4 |

-continued

| Organism | $\mu g/ml^{-1}$ (microtitre in broth) |
|---|---|
| *Bacillus subtilis* A | 0.2 |
| *Staphylococcus aureus* Oxford | ≦0.1 |
| *Staphylococcus aureus* Russell | ≦0.1 |
| *Staphylococcus aureus* 1517 | 1.6 |
| *Streptococcus faecalis* 1 | 0.8 |
| *Streptococcus pneumoniae* CN33 | ≦0.1 |
| *Streptococcus pyogenes* CN10 | ≦0.1 |
| *E. coli* ESS | 0.2 |

EXAMPLE 4

5(R,S), 6(S,R)

3-(E)-2-Aminoethylamido-ethenylthio-6-(1R,S-hydroxyethyl)-7-oxo-1-azabicyclo[3.2.0]hept-2-ene-2-carboxylate

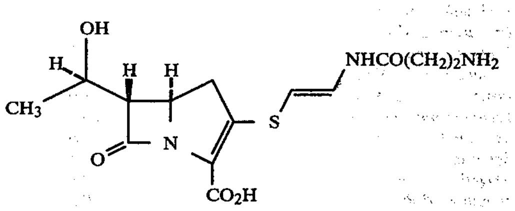

The compound was prepared as described for Example 2. The product was obtained in aqueous solution $\lambda_{max}$ ($H_2O$) 230, 308 nm.

The concentrations of this compound required to inhibit the growth of the following bacteria are given below.

| Organism | $\mu g/ml$ (microtitre in broth) |
|---|---|
| *Citrobacter freundii* | 0.8 |
| *Enterobacter cloacae* N1 | 0.8 |
| *Escherichia coli* 0111 | 0.4 |
| *Escherichia coli* JT39 | 0.4 |
| *Klebsiella aerogenes* A | ≦0.1 |
| *Proteus mirabilis* C977 | 3.1 |
| *Proteus morganii* 1580 | 1.6 |
| *Proteus rettgeri* WM16 | 1.6 |
| *Proteus vulgaris* WO91 | 1.6 |
| *Pseudomonas aeruginosa* A | 50 |
| *Salmonella typhimurium* CT10 | 1.6 |
| *Serratia marcescens* US20 | 0.4 |
| *Shigella sonnei* MB 11967 | 0.4 |
| *Bacillus subtilis* A | ≦0.1 |
| *Staphylococcus aureus* Oxford | ≦0.1 |
| *Staphylococcus aureus* Russell | ≦0.1 |
| *Staphylococcus aureus* 1517 | 3.1 |
| *Streptococcus faecalis* 1 | 3.1 |
| *Streptococcus pneumoniae* CN33 | ≦0.1 |
| *Streptococcus pyogenes* CN10 | ≦0.1 |
| *E. coli* ESS | 0.2 |

What we claim is:

1. A compound of the formula (I)

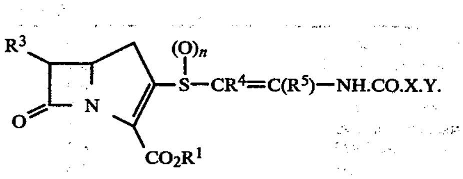
(I)

wherein $R^1$ is a group such that $CO_2R^1$ is a carboxylic acid group, a pharmaceutically acceptable salt thereof or a pharmaceutically acceptable ester thereof; $R^3$ is hydrogen or a group of formula (c):

$$—CR^6R^7R^8 \quad (c)$$

wherein $R^6$ is hydrogen, hydroxy, $—OSO_3H$ or a pharmaceutically acceptable salt thereof, $—OCOR°$ or $—OCO_2R°$ wherein R° is a hydrocarbon of 1 to 8 carbon atoms unsubstituted or substituted with halogen, alkoxy of 1 to 6 carbon atoms or nitro; $R^7$ is hydrogen or alkyl of 1-3 carbon atoms; and $R^8$ is hydrogen or alkyl of 1-3 carbon atoms; n is zero or 1; $R^4$ and $R^5$ are independently hydrogen or alkyl of 1 to 3 carbon atoms; X is alkylene of 1 to 6 carbon atoms unsubstituted or substituted by hydroxy or a carboxylic acid group or a pharmaceutically acceptable salt thereof or a pharmaceutically acceptable ester thereof; Y is amino, or substituted amino, wherein the substituent is acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms or a group $—NR^AR^B$ wherein $R^A$ and $R^B$ are independently hydrogen or alkyl of 1 to 6 carbon atoms and $R^{14}$ is hydrogen, alkyl of 1 to 6 carbon atoms.

2. A compound according to claim 1 of the formula (II):

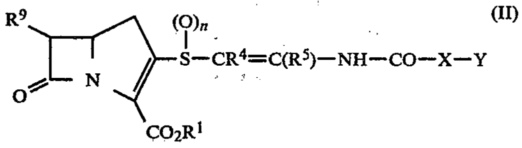
(II)

wherein n is zero or 1, $R^1$ is a group such that $CO_2R^1$ is a carboxylic acid group or a pharmaceutically acceptable salt thereof or a pharmaceutically acceptable ester thereof, $R^4$ and $R^5$ are independently hydrogen or alkyl of 1-3 carbon atoms, and X is alkylene of 1 to 6 carbon atoms unsubstituted or substituted by hydroxy or a carboxylic acid group or a pharmaceutically acceptable salt thereof or a pharmaceutically acceptable ester thereof; $R^9$ is hydrogen or $—CR^{10}R^{11}R^{12}$ wherein $R^{10}$ is hydrogen, hydroxyl, $OCOR^{13}$ or $OCOOR^{13}$ wherein $R^{13}$ is alkyl of 1 to 3 carbon atoms, phenyl, benzyl or fluorobenzyl; $R^{11}$ is hydrogen or alkyl of 1 to 3 carbon atoms; $R^{12}$ is hydrogen or alkyl of 1 to 3 carbon atoms; and Y is amino, alkylamino of 1 to 6 carbon atoms in the alkyl moiety, substituted amino wherein the substituent is acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms and $R^{14}$ is hydrogen, alkyl of 1 to 6 carbon atoms or a group $—NR^AR^B$ wherein $R^A$ and $R^B$ are independently hydrogen or alkyl of 1 to 6 carbon atoms, —NHCOZ wherein Z is lower alkyl, aryl, aryloxyalkyl or aralkyl, wherein the aryl moiety is phenyl unsubstituted or substituted by chloro, bromo, fluoro, nitro, alkyl of 1 to 3 carbon atoms or alkoxy of 1 to 3 carbon atoms and the alkyl moiety is a lower alkyl moiety.

3. A compound according to claim 2 wherein n is zero.

4. A compound according to claim 1 wherein $R^3$ is hydrogen.

5. A compound according to claim 1 wherein $R^3$ is of subformula (f) or (g):

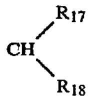
(f)

-continued or

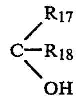

(g)

wherein $R_{17}$ is hydrogen, methyl or ethyl and $R_{18}$ is hydrogen, methyl or ethyl.

6. A compound according to claim 5 wherein $R^3$ is methyl, ethyl, isopropyl, n-propyl, α-hydroxypropyl.

7. A compound according to claim 1 wherein $R^4$ and $R^5$ are each hydrogen.

8. A compound according to claim 7 wherein the group —CH═CH—NHCO—X—Y is in the cis-configuration.

9. A compound according to claim 1 wherein X is methylene or ethylene.

10. A compound according to claim 1 wherein Y is amino.

11. The compound according to claim 1 which is 3-(Z)-2-Glycinamidoethenylthio-6-(1R-hydroxy-ethyl)-7-oxo-1-azabicyclo[3.2.0]hept-2-ene-2-carboxylate.

12. The compound according to claim 1 which is 3-(Z)-2-Aminoethylamidoethenylthio-6-(1R-hydroxyethyl)-7-oxo-1-azabicyclo[3.2.0]hept-2-ene-2-carboxylate.

13. A compound of the formula (III):

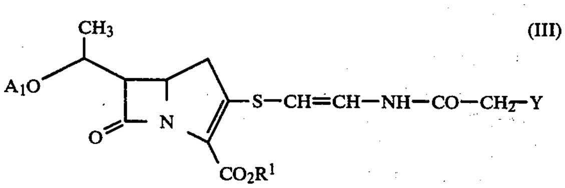

(III)

wherein Y is amino, or substituted amino, wherein the substituent is carboxylic acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms, and $R^{14}$ is hydrogen, alkyl of 1 to 6 carbon atoms or a group $—NR^AR^B$ wherein $R^A$ and $R^B$ are independently hydrogen or alkyl of 1 to 6 carbon atoms; $R^1$ is a group such that $CO_2R^1$ is a carboxylic acid group or a pharmaceutically acceptable salt thereof or a pharmaceutically acceptable ester thereof, and $A_1$ is hydrogen or acetyl.

14. A compound according to claim 13 wherein $CO_2R^1$ is a pharmaceutically acceptable salt of a carboxyl group when Y does not contain an amino or imino group.

15. A compound according to claim 13 wherein $CO_2R^1$ is an in vivo hydrolyzable ester group.

16. A compound according to claim 13 wherein $CO_2R^1$ is a phthalidyl ester group.

17. A compound according to claim 13 wherein $CO_2R^1$ is a p-nitrobenzyl ester group.

18. A compound according to claim 13 wherein Y contains an amino or imino group and the compound of the formula (III) is in the form of a zwitterion.

19. A compound of the formula (IV):

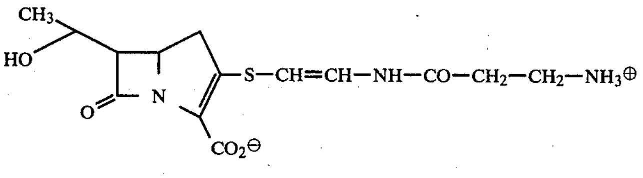

(IV)

20. A compound of the formula (V):

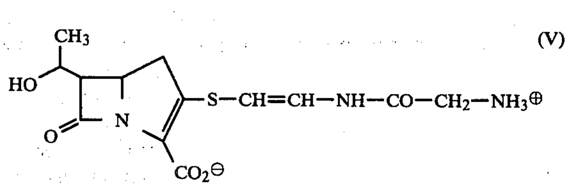

(V)

21. A pharmaceutical composition useful for treating bacterial infections in humans and animals which comprises an antibacterially effective amount of a compound of the formula (I):

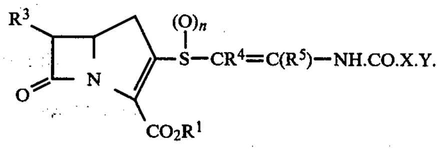

(I)

wherein $R^1$ is a group such that $CO_2R^1$ is a carboxylic acid group, a pharmaceutically acceptable salt thereof or a pharmaceutically acceptable ester thereof; $R^3$ is hydrogen or a group of formula (c):

$$—CR^6R^7R^8 \quad (c)$$

wherein $R^6$ is hydrogen, hydroxy, $—OSO_3H$ or a pharmaceutically acceptable salt thereof, —OCOR° or $—OCO_2R°$ wherein R° is a hydrocarbon of 1 to 8 carbon atoms unsubstituted or substituted with halogen, alkoxy of 1 to 6 carbon atoms or nitro; $R^7$ is hydrogen or alkyl of 1–3 carbon atoms; and $R^8$ is hydrogen or alkyl of 1–3 carbon atoms; n is zero or 1; $R^4$ and $R^5$ are independently hydrogen or alkyl of 1 to 3 carbon atoms; X is alkylene of 1 to 6 carbon atoms unsubstituted or substituted by hydroxy or a carboxylic acid group or a pharmaceutically acceptable salt thereof or a pharmaceutically acceptable ester thereof; Y is amino, or substituted amino, wherein the substituent is acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms and $R^{14}$ is hydrogen, alkyl of 1 to 6 carbon atoms or a group $—NR^AR^B$ wherein $R^A$ and $R^B$ are independently hydrogen or alkyl of 1 to 6 carbon atoms, in combination with a pharmaceutically acceptable carrier.

22. A composition according to claim 21 wherein the compound is of the formula (II):

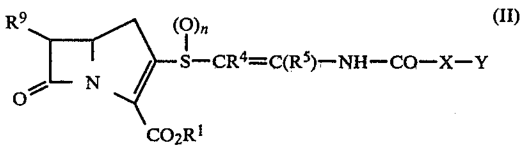
(II)

wherein n is zero or 1, $R^1$ is a group such that $CO_2R^1$ is a carboxylic acid group or a pharmaceutically acceptable salt thereof or a pharmaceutically acceptable ester thereof, $R^4$ and $R^5$ are independently hydrogen or alkyl of 1-3 carbon atoms, and X is alkylene of 1 to 6 carbon atoms unsubstituted or substituted by hydroxy or a carboxylic acid group or a pharmaceutically acceptable salt thereof or a pharmaceutically acceptable ester thereof; $R^9$ is hydrogen or $-CR^{10}R^{11}R^{12}$ wherein $R^{10}$ is hydrogen, hydroxyl, $OCOR^{13}$ or $OCOOR^{13}$ wherein $R^{13}$ is alkyl of 1 to 3 carbon atoms, phenyl, benzyl or fluorobenzyl; $R^{11}$ is hydrogen or alkyl of 1 to 3 carbon atoms; $R^{12}$ is hydrogen or alkyl of 1 to 3 carbon atoms; and Y is amino, alkylamino of 1 to 6 carbon atoms in the alkyl moiety, substituted amino wherein the substituent is acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms and $R^{14}$ is hydrogen, alkyl of 1 to 6 carbon atoms or a group $-NR^AR^B$ wherein $R^A$ and $R^B$ are independently hydrogen or alkyl of 1 to 6 carbon atoms, —NHCOZ wherein Z is lower alkyl, aryl, aryloxyalkyl or aralkyl, wherein the aryl moiety is phenyl unsubstituted or substituted by chloro, bromo, fluoro, nitro, alkyl of 1 to 3 carbon atoms or alkoxy of 1 to 3 carbon atoms and the alkyl moiety is a lower alkyl moiety.

23. A composition according to claim 21 wherein n is zero.

24. A composition according to claim 21 wherein $R^3$ is hydrogen.

25. A composition according to claim 21 wherein $R^3$ is of sub-formula (f) or (g):

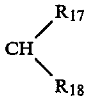
(f)

or

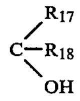
(g)

wherein $R_{17}$ is hydrogen, methyl or ethyl and $R_{18}$ is hydrogen, methyl or ethyl.

26. A composition according to claim 21 wherein $R^3$ is methyl, ethyl, isoproply, n-proply, α-hydroxypropyl.

27. A composition according to claim 21 wherein $R^4$ and $R^5$ are each hydrogen,

28. A composition according to claim 21 wherein the group —CH=CH—NHCO—X—Y is in the cis-configuration.

29. A composition according to claim 21 wherein X is methylene.

30. A composition according to claim 21 wherein Y is amino.

31. A composition according to claim 21 wherein the compound is of the formula (III):

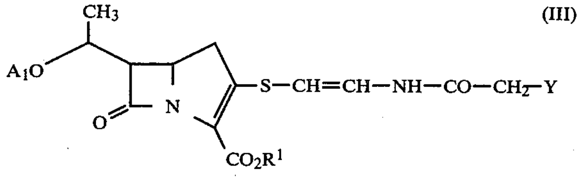
(III)

wherein Y is amino, or substituted amino, wherein the substituent is carboxylic acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms, and $R^{14}$ is hydrogen, alkyl of 1 to 6 carbon atoms or a group $-NR^AR^B$ wherein $R^A$ and $R^B$ are independently hydrogen or alkyl of 1 to 6 carbon atoms; $R_1$ is a group such that $CO_2R_1$ is a carboxylic acid group or a pharmaceutically acceptable salt thereof or a pharmaceutically acceptable ester thereof, and $A_1$ is hydrogen or acetyl.

32. A composition according to claim 31 wherein $CO_2R^1$ is a pharmaceutically acceptable salt of a carboxyl group when Y does not contain an amino or imino group.

33. A composition according to claim 31 wherein $CO_2R^1$ is an in vivo hydrolyzable ester group.

34. A composition according to claim 31 wherein $CO_2R^1$ is a phthalidyl ester group.

35. A composition according to claim 31 wherein $CO_2R^1$ is a p-nitrobenzyl ester group.

36. A composition according to claim 31 wherein Y contains an amino or imino group and the compound of the formula (III) is in the form of a zwitterion.

37. A composition according to claim 21 wherein the compound is of the formula (IV):

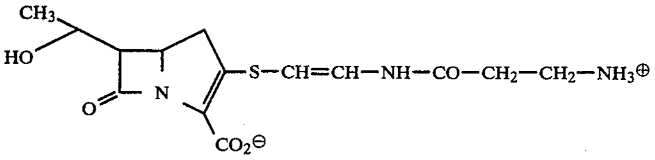
(IV)

38. A composition according to claim 21 wherein the compound is of the formula (V):

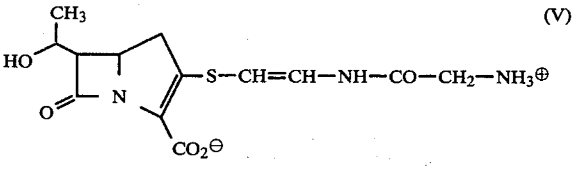
(V)

39. A composition according to claim 21 wherein the compound is 3-(Z)-2-Glycinamidoethenylthio-6-(1R-hydroxyethyl)-7-oxo-1-azabicyclo[3.2.0]hept-2-ene-2-carboxylate.

40. A composition according to claim 21 wherein the compound is 3-(Z)-2-Aminoethylamidoethenylthio-6-(1R-hydroxyethyl)-7-oxo-1-azabicyclo[3.2.0]hept-2-ene-2-carboxylate.

41. A composition according to claim 21 in oral administration form.

42. A composition according to claim 21 in parenteral administration form.

43. A composition according to claim 21 in injectable administration form.

44. A method of treating bacterial infections in humans and animals which comprises administering to a human or animal in need thereof, an antibacterially effective amount of the formula (I):

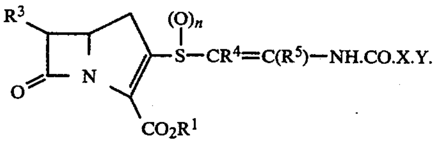

(I)

wherein $R^1$ is a group such that $CO_2R^1$ is a carboxylic acid group, a pharmaceutically acceptable salt thereof or a pharmaceutically acceptable ester thereof; $R^3$ is hydrogen or a group of formula (c):

$$—CR^6R^7R^8 \quad (c)$$

wherein $R^6$ is hydrogen, hydroxy, $—OSO_3H$ or a pharmaceutically acceptable salt thereof, $—OCOR°$ or $—O-CO_2R°$ wherein R° is a hydrocarbon of 1 to 8 carbon atoms unsubstituted or substituted with halogen, alkoxy of 1 to 6 carbon atoms or nitro; $R^7$ is hydrogen or alkyl of 1-3 carbon atoms; and $R^8$ is hydrogen or alkyl of 1-3 carbon atoms; n is zero or 1; $R^4$ and $R^5$ are independently hydrogen or alkyl of 1 to 3 carbon atoms; X is alkylene of 1 to 6 carbon atoms unsubstituted or substituted by hydroxy or a carboxylic acid group or a pharmaceutically acceptable salt thereof or a pharmaceutically acceptable ester thereof; Y is amino, or substituted amino, wherein the substituent is acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms and $R^{14}$ is hydrogen, alkyl of 1 to 6 carbon atoms or a group $—NR^AR^B$ wherein $R^A$ and $R^B$ are independently hydrogen or alkyl of 1 to 6 carbon atoms, in combination with a ~~pharmaceutically~~ acceptable carrier.

45. A method according to claim 44 wherein the compound is of the formula (II):

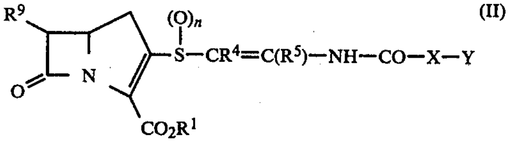

(II)

wherein n is zero or 1, $R^1$ is a group such that $CO_2R^1$ is a carboxylic acid group or a pharmaceutically acceptable salt thereof or a pharmaceutically acceptable ester thereof, $R^4$ and $R^5$ are independently hydrogen or alkyl of 1-3 carbon atoms, and X is alkylene of 1 to 6 carbon atoms unsubstituted or substituted by hydroxy or a carboxylic acid group or a pharmaceutically acceptable salt thereof or a pharmaceutically acceptable ester thereof; $R^9$ is hydrogen or $—CR^{10}R^{11}R^{12}$ wherein $R^{10}$ is hydrogen, hydroxyl, $OCOR^{13}$ or $OCOOR^{13}$ wherein $R^{13}$ is alkyl of 1 to 3 carbon atoms, phenyl, benzyl or fluorobenzyl; $R^{11}$ is hydrogen or alkyl of 1 to 3 carbon atoms; $R^{12}$ is hydrogen or alkyl of 1 to 3 carbon atoms; and Y is amino, alkylamino of 1 to 6 carbon atoms in the alkyl moiety, substituted amino wherein the substituent is acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms and $R^{14}$ is hydrogen, alkyl of 1 to 6 carbon atoms or a group $—NR^AR^B$ wherein $R^A$ and $R^B$ are independently hydrogen or alkyl of 1 to 6 carbon atoms, —NHCOZ wherein Z is lower alkyl, aryl, aryloxyalkyl or aralkyl, wherein the aryl moiety is phenyl unsubstituted or substituted by chloro, bromo, fluoro, nitro, alkyl of 1 to 3 carbon atoms or alkoxy of 1 to 3 carbon atoms and the alkyl moiety is a lower alkyl moiety.

46. A method of according to claim 44 wherein n is zero.

47. A method according to claim 44 wherein $R^3$ is hydrogen.

48. A method according to claim 44 wherein $R^3$ is of the sub-formula (f) or (g):

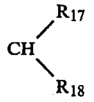

(f)

or

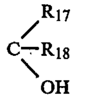

(g)

wherein $R_{17}$ is hydrogen, methyl or ethyl and $R_{18}$ is hydrogen, methyl or ethyl.

49. A method according to claim 44 wherein $R^3$ is methyl, ethyl, isoproply, n-proply, α-hydroxypropyl.

50. A method according to claim 44 wherein $R_4$ and $R_5$ are each hydrogen.

51. A method according to claim 44 wherein the group —CH=CH—NHCO—X—Y is in the cis-configuration.

52. A method according to claim 44 wherein X is methylene.

53. A method according to claim 44 wherein Y is amino.

54. A method according to claim 44 wherein the compound is of the formula (III):

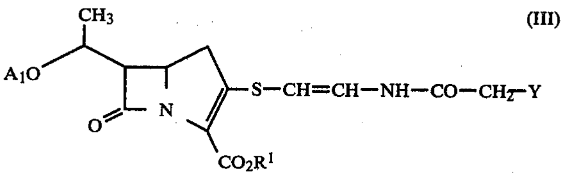

(III)

wherein Y is amino, or substituted amino, wherein the substituent is carboxylic acyl, alkyl of 1 to 6 carbon atoms or a group $=C(R^{14})NR^{15}R^{16}$ wherein $R^{15}$ and $R^{16}$ are independently hydrogen or alkyl of 1 to 6 carbon atoms, and $R^{14}$ is hydrogen, alkyl of 1 to 6 carbon atoms or a group $—NR^AR^B$ wherein $R^A$ and $R^B$ are independently hydrogen or alkyl of 1 to 6 carbon atoms; $R_1$ is a group such that $CO_2R^1$ is a carboxylic acid group or a pharmaceutically acceptable salt thereof or a pharmaceutically acceptable ester thereof, and $A_1$ is hydrogen or acetyl.

55. A method according to claim 54 wherein $CO_2R^1$ is a pharmaceutically acceptable salt of a carboxyl group when Y does not contain an amino or imino group.

56. A method according to claim 54 wherein $CO_2R^1$ is an in vivo hydrolyzable ester group.

57. A method according to claim 54 wherein $CO_2R^1$ is a phthalidyl ester group.

58. A method according to claim 54 wherein $CO_2R^1$ is a p-nitrobenzyl ester group.

59. A method according to claim 54 wherein Y contains an amino or imino group and the compound of the formula (III) is in the form of a zwitterion.

60. A method according to claim 44 wherein the compound is of the formula (IV):

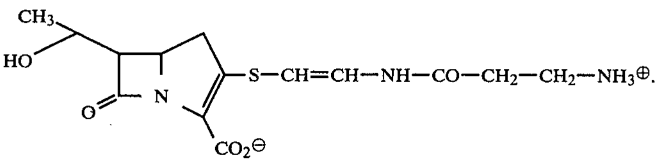

(IV)

61. A method according to claim 44 wherein the compound is of the formula (V):

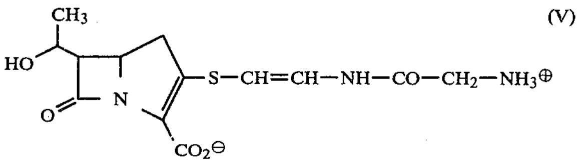

(V)

62. A method according to claim 44 wherein the compound is 3-(Z)-2-Glycinamidoethenylthio-6-(1R-hydroxyethyl)-7-oxo-1-azabicyclo[3.2.0.]hept-2-ene-2-carboxylate.

63. A method according to claim 44 wherein the compound is 3-(Z)-2-Aminoethylamidoethenylthio-6-(1R-hydroxyethyl)-7-oxo-1-azabicyclo[3.2.0.]hept-2-ene-2-carboxylate.

64. A method according to claim 44 wherein the administration is oral.

65. A method according to claim 62 wherein the administration is parenteral.

66. A method according to claim 44 wherein the administration is by injection.

* * * * *